(12) United States Patent
Zhao et al.

(10) Patent No.: US 8,280,511 B2
(45) Date of Patent: Oct. 2, 2012

(54) SYSTEMS AND METHODS FOR USE BY AN IMPLANTABLE MEDICAL DEVICE FOR DETECTING HEART FAILURE BASED ON THE INDEPENDENT INFORMATION CONTENT OF IMMITTANCE VECTORS

(75) Inventors: Wenxia Zhao, Thousand Oaks, CA (US); Dorin Panescu, San Jose, CA (US); Anders Bjorling, Solna (SE)

(73) Assignee: Pacesetter, Inc., Sylmar, CA (US)

( * ) Notice: Subject to any disclaimer, the term of this patent is extended or adjusted under 35 U.S.C. 154(b) by 1121 days.

(21) Appl. No.: 12/168,750

(22) Filed: Jul. 7, 2008

(65) Prior Publication Data

US 2010/0004712 A1  Jan. 7, 2010

(51) Int. Cl.
*A61N 1/365* (2006.01)

(52) U.S. Cl. ........... 607/17; 607/1; 607/2; 607/5; 607/6; 607/7; 607/8; 607/9; 607/11; 607/18; 607/23; 607/28; 607/30; 607/32; 607/115; 607/116; 607/119; 607/122; 607/123; 600/508; 600/509; 600/510; 600/512; 600/513; 600/526

(58) Field of Classification Search ............. 607/1–2, 607/5–9, 11, 17–18, 23, 28, 30, 32, 115–116, 607/119, 122, 123; 600/508–510, 512–513, 600/526

See application file for complete search history.

(56) References Cited

U.S. PATENT DOCUMENTS

| | | | |
|---|---|---|---|
| 5,476,483 A | 12/1995 | Bornzin et al. | |
| 5,842,997 A | 12/1998 | Verrier et al. | |
| 5,921,940 A | 7/1999 | Verrier et al. | |
| 6,128,534 A | 10/2000 | Park et al. | |
| 6,132,380 A | 10/2000 | Cohen et al. | |
| 6,249,705 B1 | 6/2001 | Snell | |
| 6,473,640 B1 * | 10/2002 | Erlebacher | 600/547 |
| 6,480,733 B1 | 11/2002 | Turcott | |
| 6,512,952 B2 | 1/2003 | Stahmann et al. | |
| 6,512,953 B2 | 1/2003 | Florio et al. | |
| 6,527,729 B1 | 3/2003 | Turcott | |
| 6,572,557 B2 | 6/2003 | Tchou et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,658,292 B2 | 12/2003 | Kroll et al. | |
| 6,741,885 B1 | 5/2004 | Bornzin et al. | |
| 6,748,261 B1 | 6/2004 | Kroll et al. | |
| 6,922,587 B2 | 7/2005 | Weinberg | |
| 6,942,622 B1 | 9/2005 | Turcott | |
| 7,022,077 B2 | 4/2006 | Mourad et al. | |
| 7,076,300 B1 | 7/2006 | Kroll et al. | |
| 7,123,954 B2 | 10/2006 | Narayan et al. | |
| 7,171,268 B1 | 1/2007 | Kroll et al. | |
| 7,272,436 B2 | 9/2007 | Gill et al. | |
| 7,274,961 B1 | 9/2007 | Kroll et al. | |
| 2004/0172080 A1 | 9/2004 | Stadler et al. | |

* cited by examiner

*Primary Examiner* — Carl H Layno
*Assistant Examiner* — Deborah Malamud

(57) ABSTRACT

Techniques are provided for detecting heart failure or other medical conditions within a patient using an implantable medical device, such as pacemaker or implantable cardioverter/defibrillator, or external system. In one example, physiological signals, such as immittance-based signals, are sensed within the patient along a plurality of different vectors, and the amount of independent informational content among the physiological signals of the different vectors is determined. Heart failure is then detected by the implantable device based on a significant increase in the amount of independent informational content among the physiological signals. In response, therapy may be controlled, diagnostic information stored, and/or warning signals generated. In other examples, at least some of these functions are performed by an external system.

31 Claims, 9 Drawing Sheets

SYSTEMS AND METHODS FOR USE BY AN IMPLANTABLE MEDICAL DEVICE FOR DETECTING HEART FAILURE BASED ON THE INDEPENDENT INFORMATION CONTENT OF IMMITTANCE VECTORS

FIELD OF THE INVENTION

The invention generally relates to implantable medical devices, such as pacemakers or implantable cardioverter/defibrillators (ICDs) and, in particular, to techniques for detecting and tracking heart failure or other medical conditions within patients in which such devices are implanted.

BACKGROUND OF THE INVENTION

Heart failure is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles (particularly the left ventricle) to grow in thickness in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

The current standard treatment for heart failure is typically centered on medical treatment using angiotensin converting enzyme (ACE) inhibitors, diuretics, beta-blockade, and digitalis. Cardiac resynchronization therapy (CRT) may also be employed, if a biventricular pacing device is implanted. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing."

In view of the potential severity of heart failure, it is highly desirable to detect the onset of heart failure within a patient and to track the progression thereof so that appropriate therapy can be provided. Many patients suffering heart failure already have pacemakers or ICDs implanted therein or are candidates for such devices. Accordingly, it is desirable to provide such devices with the capability to automatically detect and track heart failure.

At least some techniques have been developed for detecting heart failure and controlling responsive therapy that exploit electrical immittance signals (i.e. impedance or admittance signals) detected within the patient. See, e.g., U.S. patent application Ser. No. 11/558,194, of Panescu et al., filed Nov. 9, 2006, entitled "Closed-Loop Adaptive Adjustment of Pacing Therapy based on Cardiogenic Impedance Signals Detected by an Implantable Medical Device"; and U.S. patent application Ser. No. 12/127,963, of Wenzel et al., filed May 28, 2008, entitled "System and Method for Estimating Electrical Conduction Delays from Immittance Values Measured using an Implantable Medical Device." Particularly effective techniques for calibrating immittance-based techniques are set forth in: U.S. patent application Ser. No. 11/559,235, by Panescu et al., now U.S. Pat. No. 7,794,404 entitled "System and Method for Estimating Cardiac Pressure Using Parameters Derived from Impedance Signals Detected by an Implantable Medical Device" and in U.S. patent application Ser. No. 12/109,304, by Gutfinger et al., filed Apr. 24, 2008 entitled "System and Method for Calibrating Cardiac Pressure Measurements Derived from Signals Detected by an Implantable Medical Device."

In particular, techniques are described therein that exploit immittance signals to estimate electrical or mechanical conduction delays within the heart of the patient, which are, in turn, used to detect or track heart failure. Techniques are also described therein that exploit immittance signals to directly estimate cardiac pressure values within chambers of the heart of the patient, which are, in turn, used to detect or track heart failure.

Although the techniques are effective, it would be desirable to provide alternative techniques for detecting heart failure that exploit immittance signals measured within a patient, but which do not rely on cardiac pressure estimates or conduction delay estimates. It is to this end that aspects of the present invention are primarily directed.

SUMMARY OF THE INVENTION

In an exemplary embodiment, a method is provided for use with an implantable medical device for implant within a patient, such as pacemaker or ICD. Briefly, physiological signals are sensed within the patient along a plurality of different vectors and an amount of independent informational content among the physiological signals of the different vectors is determined. At least one function is then controlled based on the amount of independent informational content among the physiological signals of the different vectors. For example, therapy may be controlled, diagnostic information may be stored, and/or warning signals may be generated, particularly if a change in the amount of independent informational content is indicative of the onset of a medical condition such as heart failure. In some implementations, all of the steps are performed by the implanted device. In other implementations, at least some of the steps are performed by an external system, such as device programmer, beside monitor, or computer server or website. In particular, in some implementations, the physiological signals are sensed or measured by the implanted device for transmission to an external system, which determines the amount of independent informational content among the physiological signals of the different vectors, generates diagnostics, controls therapy, etc.

In an illustrative embodiment wherein the various steps are performed by the implantable device, the device is equipped to measure immittance signals (i.e. impedance or admittance signals) between various pacing/sensing electrodes implanted on or within the heart. A set of sensing vectors is selected whereby an increase in the amount of independent informational content among the immittance signals is representative of a decrease in hemodynamic equilibrium within the patient brought on by heart failure. In this regard, within a healthy or stable subject, the amount of independent informational content among immittance signals measured along different vectors trends within a stable range based mainly on the common/haemostatic status of the patient. However, the onset or progression of heart failure causes the equilibrium to be broken such that the independent informational content of each vector becomes predominant. Accordingly, a value representative of the independent informational content among the immittance signal vectors can be used to detect the onset or progression of heart failure or other conditions affecting the hemodynamic equilibrium of the patient.

In one particular example, the implanted device includes a set of biventricular pacing/sensing leads having, at least, a left ventricular (LV) ring electrode, a right ventricular (RV) ring electrode, and a right atrial (RA) ring electrode. The device selects pair of sensing vectors—such as the LV ring-to-RA ring and LV ring-to-RV ring sensing vectors—to measure electrical impedance. The device tracks and records pairs of impedance values (x,y) over a period of time from one to thirty-one days, with one value of each (x,y) pair derived from the LV ring-to-RA ring vector and the other derived from the LV ring-to-RV vector. The device then determines an inter-vector cross-correlation coefficient from the impedance values (x,y) of the two different vectors. The amount of independent informational content of the two vectors is then derived from the cross-correlation coefficient.

For example, the device may be programmed to determine the cross-correlation coefficient from the pair of impedance signals by calculating:

$$r = \frac{n\sum xy - (\sum x)(\sum y)}{\sqrt{n(\sum x^2) - (\sum x)^2}\sqrt{n(\sum y^2) - (\sum y)^2}}$$

where n is the number of pairs of data recorded. When there is minimal independent informational content between the two impedance vectors, r is close to ±1. When there is substantial independent informational content, r is close to 0. Hence, the device determines the amount of independent informational content by determining how close the cross-correlation coefficient is to 0.

The implantable device, for example, may be programmed to calculate an index representative of the total amount of independent informational content by evaluating the numerical accumulation of the cross-correlation over the period of time during which the impedance data is collected (e.g. over the last one to thirty-one days.) The closer the index trends toward 0, the more likely the hemodynamic equilibrium of the patient has been affected by heart failure or other conditions. Accordingly, the index may be compared against one or more threshold values indicative of the onset or progression of heart failure. Depending upon the particular implementation, suitable warning signals are triggered, diagnostics are recorded and therapy is controlled. If the device is equipped to perform CRT, such therapy may be automatically activated or adjusted based on the detection of the onset or progression of heart failure.

In other examples, rather than using only one pair of sensing vectors, groups of sensing vectors may instead be selected, with one or more indices calculated so as to be representative of the overall amount of independent informational content among the various groups of vectors. In particular, for detecting heart failure, the following set of three vector pairs is preferred: (1) LV ring to RA ring vs. LV ring to RV ring, (2) LV ring to RA ring vs. LV ring to Case, and (3) LV ring to RV ring vs. LV ring to Case.

By exploiting correlation coefficients or other values representative of the amount of independent informational content within immittance vector signals, various advantages are realized. For example, the correlation coefficients are independent from the immittance baseline of an immittance-measuring configuration. That is, low immittance does not affect the correlation coefficients. In addition, the correlation coefficients typically change more significantly (e.g. by more than 30%) during heart failure exacerbation, as compared with only a 10-15% change in immittance measurements. As such, it is typically easier to detect heart failure by exploiting correlation coefficients than by using detection techniques that instead directly exploit immittance measurements. Still further, the use of correlation coefficients may allow for earlier detection of heart failure than other immittance-based techniques.

Various other medical conditions besides heart failure are also detectable using independent information content-based techniques. In general, any medical condition that affects the independent informational content of different physiological signal vectors is potentially detectable. As with heart failure, any medical condition that affects the hemodynamic equilibrium of the patient will also tend to affect the independent informational content of different physiological signal vectors (at least along vectors through the particular tissues that are affected by changes in the hemodynamic equilibrium). Hence, any medical condition affecting hemodynamic equilibrium is potentially detectable using independent informational content-based detection techniques. Furthermore, different medical conditions will typically affect the independent informational content of physiological vectors somewhat differently, thus allowing the implantable device to distinguish among different medical conditions. Moreover, different sets of sensing vectors may be exploited to distinguish among different medical conditions, since different sensing vectors typically exhibit differing amounts of change in independent informational content depending upon the medical condition.

BRIEF DESCRIPTION OF THE DRAWINGS

The above and further features, advantages and benefits of the invention will be apparent upon consideration of the descriptions herein taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
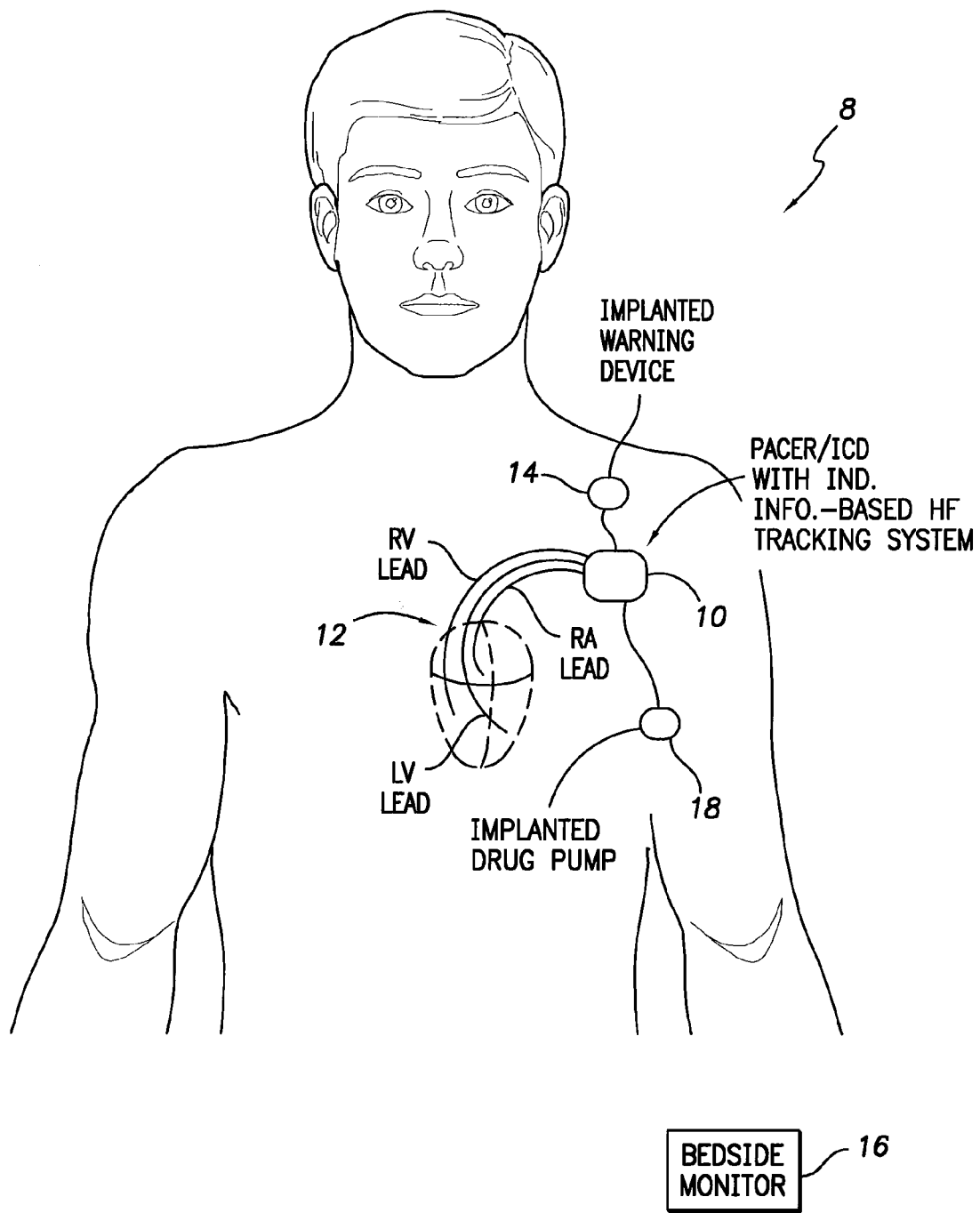
FIG. 1 illustrates pertinent components of an implantable medical system having a pacer/ICD equipped with an independent informational content-based heart failure (HF) tracking system.

FIG. 1 illustrates an implantable medical system 8 capable of detecting heart failure or other medical conditions based on the amount of independent informational content along different physiological signal sensing vectors and also capable of controlling delivery of appropriate warnings and therapy in response thereto. To this end, a pacer/ICD 10 (or other implantable medical device) measures physiological signals, such as impedance/admittance signals, via a set of cardiac pacing/sensing leads 12. In FIG. 1, a stylized representation of three leads is provided. A more thorough and anatomically correct illustration of the leads is provided in FIG. 8 (described below). Physiological signals are detected or measured using various combinations of electrodes on the leads (as well as a device can electrode connected to the device case or housing), which collectively provide various sensing vectors passing through different portions of the heart and thorax of the patient. The amount of independent informational content among the physiological signals of the various sensing vectors is evaluated and used to detect the onset or progression of heart failure or other conditions. Warning signals may be generated, diagnostic information stored, and/or therapy controlled.

For example, if the amount of independent informational content among the sensing vectors exceeds a threshold indicative of the onset of heart failure, warning signals are generated to warn the patient, using either an internal warning device 14 or an external bedside monitor 16. Internal warning device 14 may be a vibrating device or a "tickle" voltage device that, in either case, provides perceptible stimulation to the patient to alert the patient so that the patient may consult a physician. In one example, once the tickle warning is felt, the patient positions an external handheld warning device above his or her chest. The handheld device receives short-range telemetry signals from the implanted device and provides audible or visual verification of the warning signal. The handheld warning device thereby provides confirmation of the warning to the patient, who might be otherwise uncertain as to the reason for the internally generated warning signal. For further information regarding this type of warning/notification technique, see U.S. Pat. No. 7,272,436, to Gill et al.

If a bedside monitor is provided, the bedside monitor provides audible or visual alarm signals to alert the patient as well as textual or graphic displays. In addition, diagnostic information pertaining to heart failure is transferred to the bedside monitor or is stored within the pacer/ICD for subsequent transmission to an external programmer (not shown in FIG. 1) for review by a physician or other medical professional. External programmers are typically used only during follow-up sessions with the patient wherein a clinician downloads information from the implanted device, reviews the information and then adjusts the control parameters of the implanted device, if needed, via the programmer. Bedside monitors typically download information more frequently, such as once per evening and can be equipped to relay the most pertinent information to the patient's physician via a communication network. In any case, the physician may then prescribe any other appropriate therapies to address the condition. The physician may also adjust the operation of the pacer/ICD to activate, deactivate or otherwise control any therapies that are automatically applied. The bedside monitor may be directly networked with a centralized computing system, such as the HouseCall™ system or the Merlin.Net system of St. Jude Medical, for immediately notifying the physician of any significant increase in LAP. Networking techniques for use with implantable medical systems are set forth, for example, in U.S. Pat. No. 6,249,705 to Snell, entitled "Distributed Network System for Use with Implantable Medical Devices."

CRT therapy or other forms of electrical cardiac rhythm management therapy may be initiated and controlled by the pacer/ICD based on the amount of independent informational content of the physiological signal vectors. Techniques for performing CRT are discussed in the patents to Mathis et al., Kramer et al., to Stahmann et al., cited above. CRT parameters may be adaptively adjusted based on the physiological signals to improve the effectiveness of CRT using techniques set forth in the Panescu et al. patent application, "Closed-Loop Adaptive Adjustment of Pacing Therapy based on Cardiogenic Impedance Signals Detected by an Implantable Medical Device," cited above.

Other forms of therapy may be additionally or alternatively controlled by the pacer/ICD in response to changes in the amount of independent informational content of the physiological signal vectors. In this regard, if the implanted system is equipped with a drug pump 18, appropriate medications may be automatically administered upon detection of a significant increase in the amount of independent informational content of the physiological signal vectors due to heart failure. For example, heart failure medications may be delivered directly to the patient via the drug pump, if warranted. Alternatively, if a drug pump is not available, the patient may be provided with instructions (generated based on the amount of independent informational content of the physiological signal vectors) as to what dosage to take for various heart failure medications. As noted, exemplary heart failure medications include angiotensin-converting enzyme (ACE) inhibitors such as captopril, enalapril, lisinopril and quinapril, diuretics, digitalis, nitrates, and other compounds. Depending upon the particular medication, alternative compounds (e.g., intravenous or subcutaneous agents) may be required for use in connection with an implantable drug pump. Routine experimentation may be employed to identify medications for treatment of heart failure or other conditions that are safe and effective for use in connection with an implantable drug pump. Dosages may be titrated based upon the severity of heart failure. Various techniques may be employed to confirm the detection of heart failure (or other medical conditions) made by the pacer/ICD before warnings are generated of any therapy is delivered.

Additionally, the pacer/ICD performs various standard operations, such as delivering demand based atrial or ventricular pacing, overdrive pacing therapy, antitachycardia pacing (ATP). The pacer/ICD also monitors for atrial or ventricular fibrillation and delivers cardioversion or defibrillation shocks in response thereto.

Hence, FIG. 1 provides an overview of an implantable medical system capable of detecting heart failure or other conditions based on the amount of independent informational content among different physiological signal vectors, delivering any appropriate warning/notification signals, and selectively delivering medications, when warranted. Embodiments may be implemented that do not necessarily perform all of these functions. For example, embodiments may be implemented that detect heart failure but do not automatically initiate or adjust therapy. Moreover, systems provided in accordance with the invention need not include all of the components shown in FIG. 1. In many cases, for example, the system will include only a pacer/ICD and its leads. Implantable warning devices and drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention.

In addition, note that the particular locations of the implanted components shown in FIG. 1 are merely illustrative and may not necessarily correspond to actual implant locations. Although internal signal transmission lines provided are illustrated in FIG. 1 for interconnecting the various implanted components, wireless signal transmission may alternatively be employed.

Overview of Independent Informational Content-Based Techniques

Figure 2:
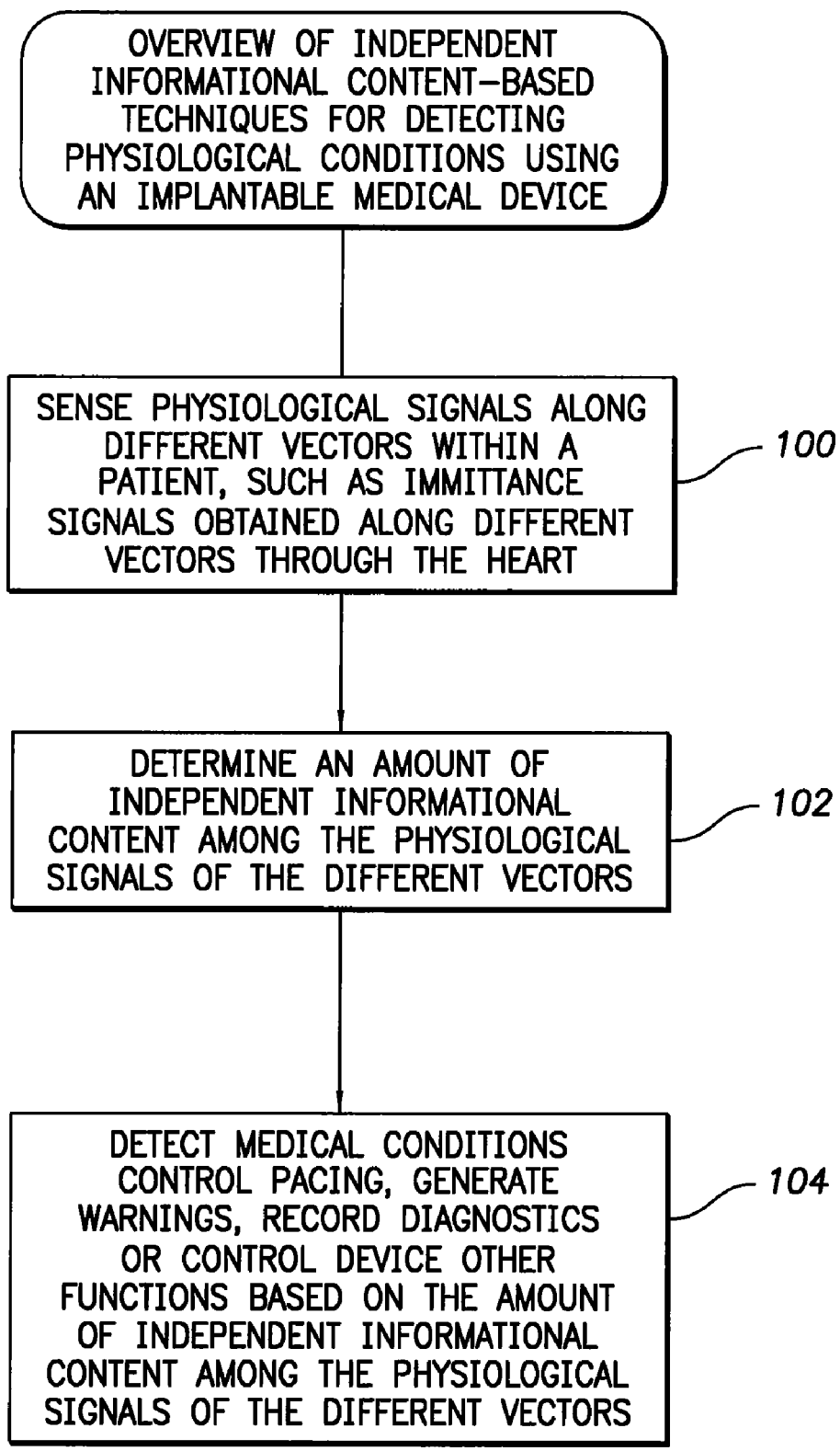
FIG. 2 provides an overview of the method for tracking heart failure and controlling device functions performed by the system of FIG. 1, which exploits the amount of independent informational content among a set of physiological signal sensing vectors.

FIG. 2 provides a broad of the overview of independent information content-based techniques that may be performed by the pacer/ICD of FIG. 1 or other suitable device. Briefly, beginning at step 100, the pacer/ICD senses or measures physiological signals along different vectors within a patient, such as vectors through the heart and lungs of the patient. At step 102, the pacer/ICD determines the amount of independent informational content among the physiological signals of the different vectors. As will be explained below, inter-vector cross-correlation techniques may be exploited to evaluate the amount of independent informational content. However, in general, any technique suitable for evaluating the amount of independent informational content among differing signal vectors can be used.

At step 104, the pacer/ICD then detects medical conditions, controls pacing, generates warnings, records diagnostics or controls device other functions based on the amount of independent informational content among the physiological signals of the different vectors. That is, in general, the pacer/ICD controls at least one device function based on the amount of independent informational content among the physiological signals of the different vectors. Insofar as detecting medical conditions are concerned, the device function that is controlled at step 104 may include the generation of a signal indicative of detection of the medical condition. The signal can be one of the aforementioned warning signals or can merely be, e.g., an internal signal generated by the microprocessor of the pacer/ICD for internal transmission and processing within the pacer/ICD.

In many of the examples described herein, the technique of FIG. 2 is exploited to detect heart failure. When the technique is employed for detecting heart failure, the physiological signal sensed at step 100 is preferably an immittance-based parameter, such as impedance (Z) or admittance (Y), or related electrical signals such as conductance (G) or resistance (R), measured along vectors through the heart and thorax. Note that these electrical parameters are related. Admittance is the numerical reciprocal of impedance. Conductance is the numerical reciprocal of resistance. In general, impedance and admittance are vector quantities, which may be represented by complex numbers (having real and imaginary components.) Unless otherwise noted, only the real portion of the impedance or admittance vector is exploited within the equations provided herein. The real component of impedance is resistance. The real component of admittance is conductance. Hence, when exploiting only the real components of these values, conductance can be regarded as the reciprocal of impedance. Likewise, when exploiting only the real components, admittance can be regarded as the reciprocal of resistance.

Otherwise routine experimentation may be employed to identify the particular immittance sensing vectors appropriate for detecting heart failure based on the amount of independent informational content of the sensing vectors. Although immittance-based signals (or related electrical signals) are generally preferred for use in detecting heart failure, other physiological signals may potentially be employed for detecting heart failure. Otherwise routine experimentation may be employed to identify other physiological signals or parameters that might be suitable for detecting heart failure, and for identifying the particular sensing vectors for use with those physiological signals. Various other medical conditions are also detectable using independent information content-based techniques. Again, otherwise routine experimentation may be employed to identify particular medical conditions suitable for independent information-based detection and for identifying the particular physiological signals and the particular sensing vectors appropriate in each case.

In addition to heart failure, another medical condition that is particularly well-suited for detection via the amount of independent informational content of physiological vectors is pulmonary edema. Pulmonary edema is a swelling and/or fluid accumulation in the lungs often caused by heart failure. Briefly, the poor cardiac function resulting from heart failure can cause blood to back up in the lungs, thereby increasing blood pressure in the lungs. The increased pressure pushes fluid—but not blood cells—out of the blood vessels and into lung tissue and air sacs. This can cause severe respiratory problems and, left untreated, can be fatal. Pulmonary edema is usually associated with relatively severe forms of heart failure and is often asymptomatic until the edema itself becomes severe, i.e. the patient is unaware of the pulmonary edema until it has progressed to a near fatal state when respiration suddenly becomes quite difficult. Hence, early detection is important. As with heart failure, pulmonary edema affects the hemodynamic equilibrium of the patient causing the amount of independent informational content of selected physiological signal vectors to increase. However, the particular effect on the amount of independent informational content caused by pulmonary edema is generally different from that of heart failure, since pulmonary edema principally affects the lungs rather than the heart. Hence, pulmonary edema can be distinguished from heart failure.

Not all medical conditions are detectable based on the independent informational content of physiological signals. Any medical condition, though, that affects the independent informational content of different physiological signal vectors is potentially detectable via the general technique of FIG. 1. As already noted, medical conditions that affect the hemodynamic equilibrium of the patient also tend to affect the independent informational content of different physiological signal vectors (at least along vectors through those tissues that are affected by changes in the hemodynamic equilibrium). Hence, any medical condition affecting hemodynamic equilibrium is potentially detectable using independent informational content-based detection techniques. Also, as noted, different medical conditions will typically affect the independent informational content of physiological vectors somewhat differently, thus allowing the pacer/ICD to distinguish or discriminate among different medical conditions. Also, typically, different sets of sensing vectors may be exploited to distinguish or discriminate among different medical conditions, since different sensing vectors will typically exhibit differing amounts of change in independent informational content depending upon the medical condition.

Inter-Vector Cross-Correlation Impedance-Based Example

Figure 3:
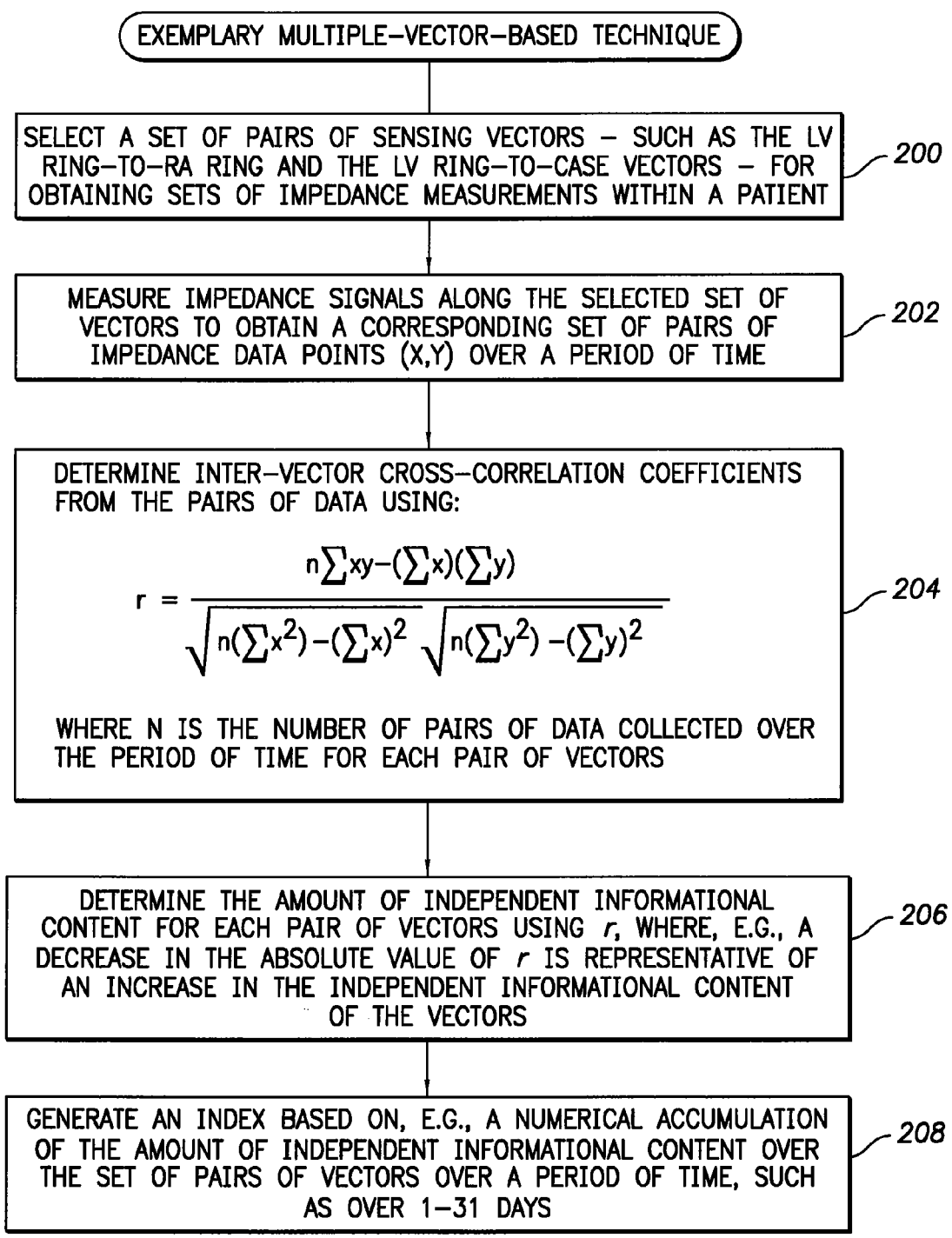
FIG. 3 illustrates an illustrative embodiment of the general technique of FIG. 2 wherein inter-vector cross-correlation is exploited to evaluate the amount of independent informational content among impedance measurements obtained along different sensing vectors through the heart.
Figure 4:
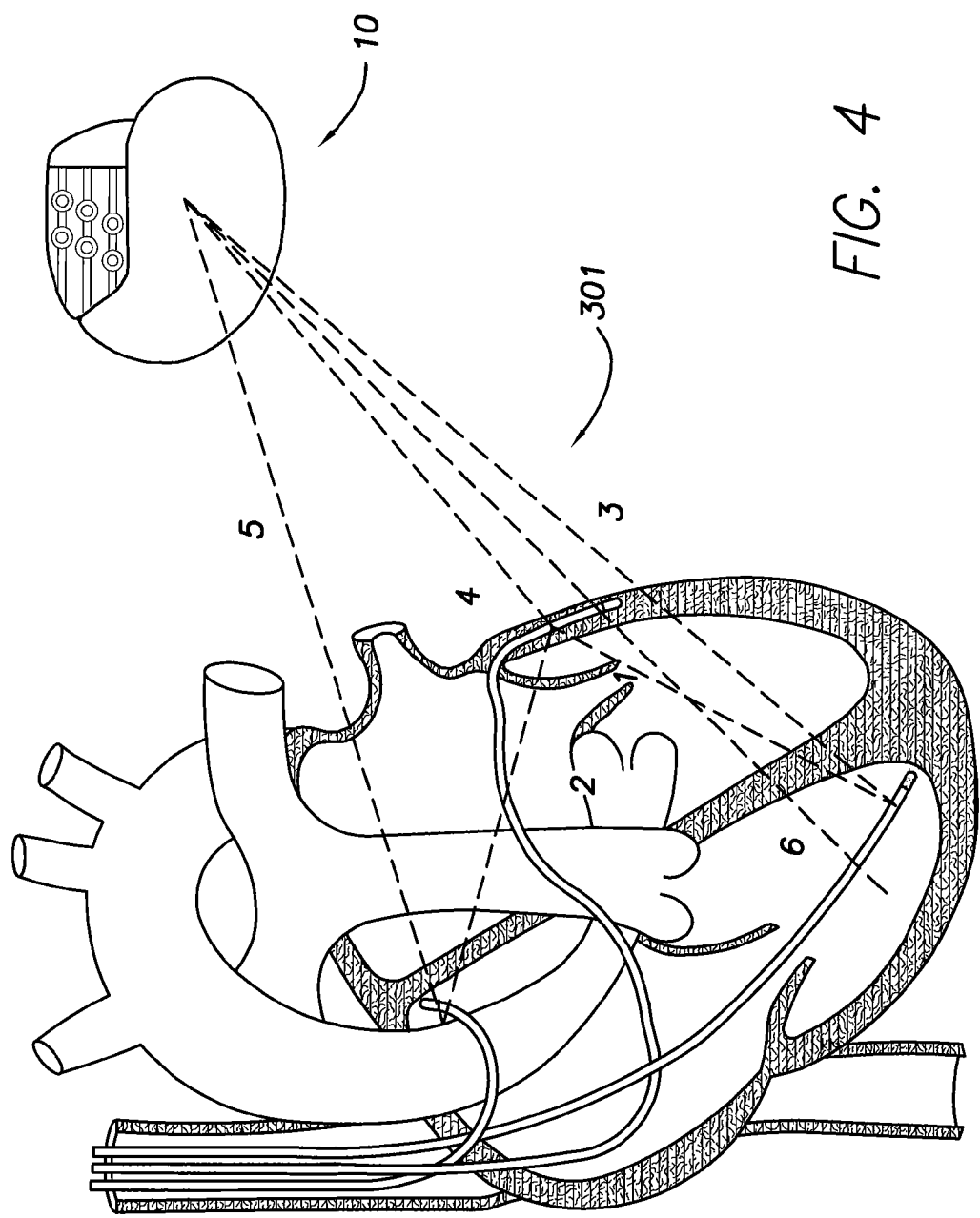
FIG. 4 provides a stylized representation of chamber of the heart of FIG. 1 and particularly illustrates various impedance vectors that may be exploited to measure impedance for use with the technique of FIG. 3.

Turning now to FIGS. 3-7, an exemplary technique exploiting the inter-vector cross-correlation of impedance vectors will be described. Beginning at step 200 of FIG. 3, the pacer/ICD selects a set of pairs of sensing vectors for obtaining impedance measurements within a patient. Various candidate vectors 301 are shown in FIG. 4. The examples specifically illustrated in FIG. 4 include: 1: LV ring to RV ring; 2. LV ring to RA ring; 3. RV ring to case; 4. LV ring to case; 5. RA ring to case; and 6. RV coil to case. From these vectors, a set of vector pairs is selected for obtaining impedance measurements, such as the set consisting of:

(1) LV ring to RA ring vs. LV ring to RV ring;
(2) LV ring to RA ring vs. LV ring to Case; and
(3) LV ring to RV ring vs. LV ring to Case.

Figure 5:
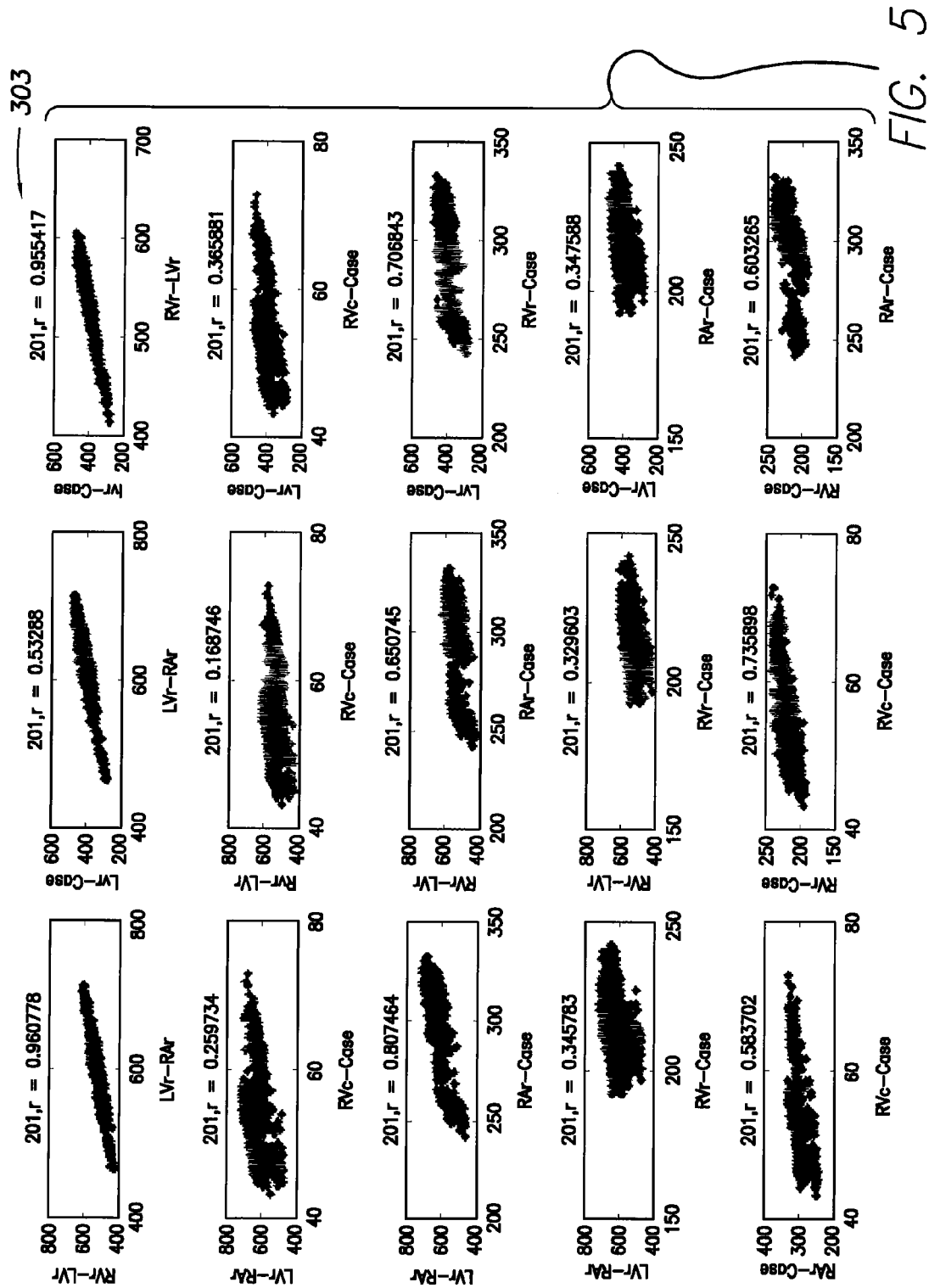
FIG. 5 provides exemplary 2-D scatter plots for impedance measurements derived from fifteen different pairs of sensing vectors, which illustrate the types of variations within information content that can be exploited by the method of FIG. 3 to detect heart failure.

FIG. 5 illustrates a set of 2-D scatter plots 303 for the impedance of all the fifteen pairs of possible impedance configurations that can be obtained from the six vectors of FIG. 4. The 2-D scatter plots were derived from impedance data obtained from a human test subject without heart failure. The first three pairs of LV ring-based configurations shown in the figure (i.e. vector pairs (1), (2) and (3) listed immediately above) have correlation coefficients r greater than 90%, indicating very little independent informational content, in accordance with the hemodynamic stability associated with a lack of heart failure. The other pairs of impedance configurations have lower correlation coefficients, indicating a greater amount of independent informational content, despite the lack of heart failure. Accordingly, the plots of FIG. 5 indicate that the aforementioned LV ring-based configurations are preferred for use in detecting heart failure (since they have very little independent informational content in the absence of heart failure.)

Returning to FIG. 3, at step 202, the pacer/ICD then measures impedance signals along each of the vectors to obtain sets of pairs of impedance data (x,y) over a selected period of time, such over a period of one to thirty-one days. That is, a pair of impedance data points $(x_1,y_1)$ is obtained for the first selected vector pair (i.e. "LV ring to RA ring vs. LV ring to RV ring") at each point in time at which impedance measurements are made. In one example, the pacer/ICD is programmed to collect impedance measurements every two hours. Another pair of impedance data points $(x_2,y_2)$ is also obtained for the second selected vector pair (i.e. "LV ring to RA ring vs. LV ring to Case") at each point in time at which impedance measurements are made. Yet another pair of impedance data points $(x_3,y_3)$ is also obtained for the third selected vector pair (i.e. "LV ring to RV ring vs. LV ring to Case") at each point in time at which impedance measurements are made. The various pairs of data collected over the selected time period are stored in device memory. That is, the measured impedance values and corresponding time stamps for the measurements for each configuration are saved in the device memory.

Preferably, a tri-phasic impedance pulse waveform is employed to measure the impedance signals. The tri-phasic waveform is a frequency-rich, low energy waveform that provides a net-zero charge and a net-zero voltage. An exemplary tri-phasic pulse waveform is described in detail in U.S. patent application Ser. No. 11/558,194, cited above.

At step 204, the pacer/ICD then determines inter-vector cross-correlation coefficients from each of the pairs of data using the following general equation:

$$r = \frac{n\sum xy - (\sum x)(\sum y)}{\sqrt{n(\sum x^2) - (\sum x)^2} \sqrt{n(\sum y^2) - (\sum y)^2}} \quad (1)$$

where n is the number of pairs of data collected over the selected period of time for a given pair of impedance vectors. That is, the equation is separately solved for each of the three pairs of vectors—(1), (2) and (3)—using the n data pairs obtained for each of those vectors so as to yield three coefficients $r_1$, $r_2$, and $r_3$. Hence, for each time stamp, a correlation coefficient is calculated for two groups of impedance measurements during a predetermined time window before the time stamp. Thus, correlation coefficients are obtained for each time stamp.

Note that, in equation (1), "x" and "y" are used to generally represent the various pairs of data (i.e. $x_1,y_1$, $x_2,y_2$, and $x_3,y_3$). Note also that, when using equation (1), if x and y have a strong positive correlation, r is close to +1. If there is no linear correlation or a weak linear correlation, r is close to 0. If X and Y have a strong negative linear correlation, r is close to −1. Hence, an r value close to 0 is representative of a significant amount of independent informational content. An r value close to +1 or close to −1 is representative of a lack of independent informational content. (This equation is the same equation used to calculate the correlation coefficients shown in FIG. 5.)

At step 206, the pacer/ICD determines the amount of independent informational content for each pair of vectors using r, where, e.g., a decrease in the absolute value of r is representative of an increase in the independent informational content of the vectors. That is, the closer r is to zero, the greater the amount of independent informational content between each pair of impedance vectors.

At step 208, the pacer/ICD generates an index based on, e.g., a combination of the amount of independent informational content over a period of time, such as over 1-31 days, over the selected set of vector pairs. That is, at step 208, the three separate coefficients obtained for each of the three pairs of vectors may be combined to yield a single index representative of the overall amount of independent informational content. The index may, for example, be the average of the three individual coefficients. In some examples, changes in the index are accumulated over a period of time. In any case, in the absence of heart failure or other conditions affecting hemodynamic equilibrium, the index stays within a fairly narrow range.

Figure 6:
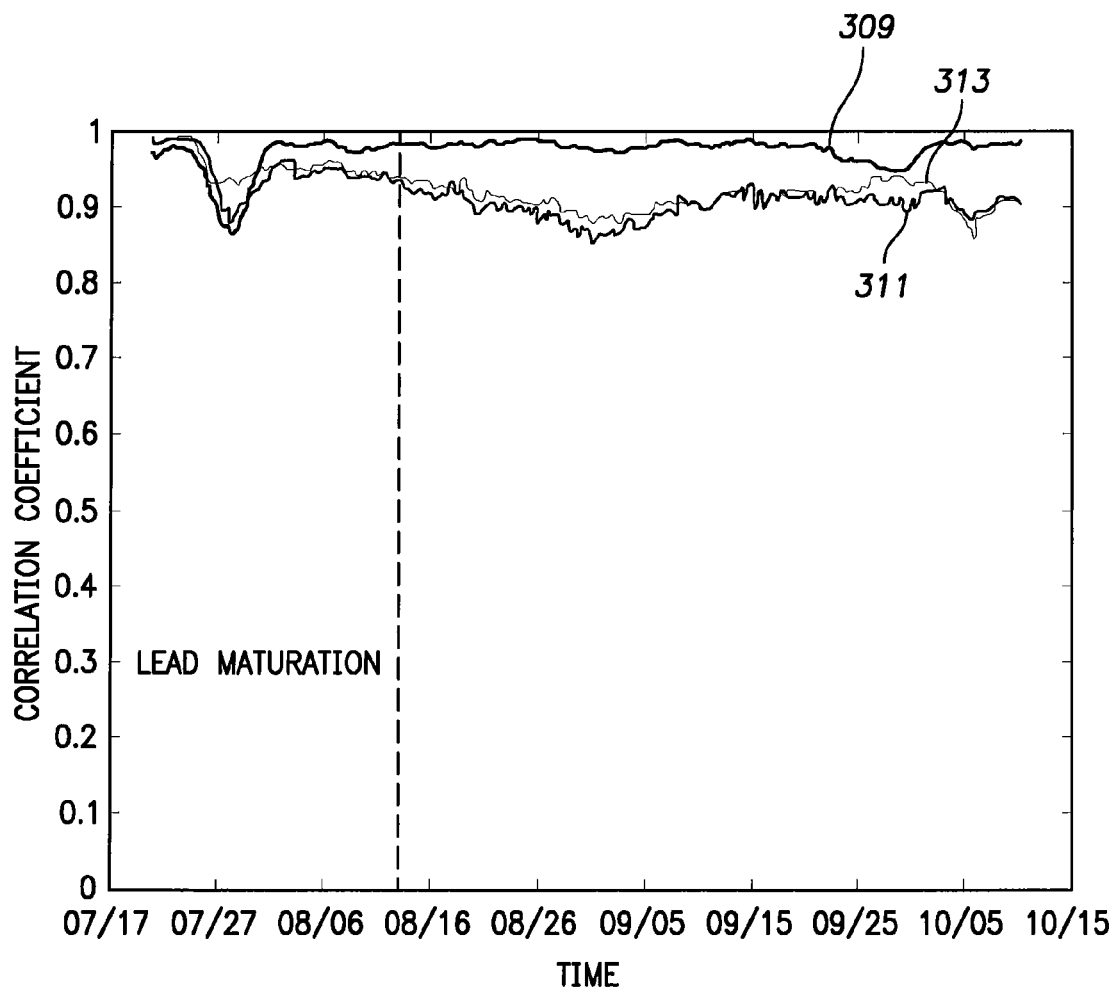
FIG. 6 provides exemplary graphs illustrating changes over time in the information content of impedance vectors for a patient without heart failure.

FIG. 6 illustrates the (non-accumulated) correlation coefficients r for each of the three preferred LV ring-based vector combinations for a first patient. More specifically, graph 309 illustrates $r_1$ for the "LV ring to RA ring vs. LV ring to RV ring" combination. Graph 311 illustrates $r_2$ for the "LV ring to RA ring vs. LV ring to Case" combination. Graph 313 illustrates $r_3$ for the "LV ring to RV ring vs. LV ring to Case" combination. Following an initial lead maturation phase, the correlation coefficients are stable around 90% or above. Hence, no heart failure is detected for this patient. Although FIG. 6 does not specifically illustrate a combined index, it can be appreciated that an index representative of a combination of the three coefficients $r_1$, $r_2$ and $r_3$ would likewise remain stable and relatively close to 100%.

Figure 7:
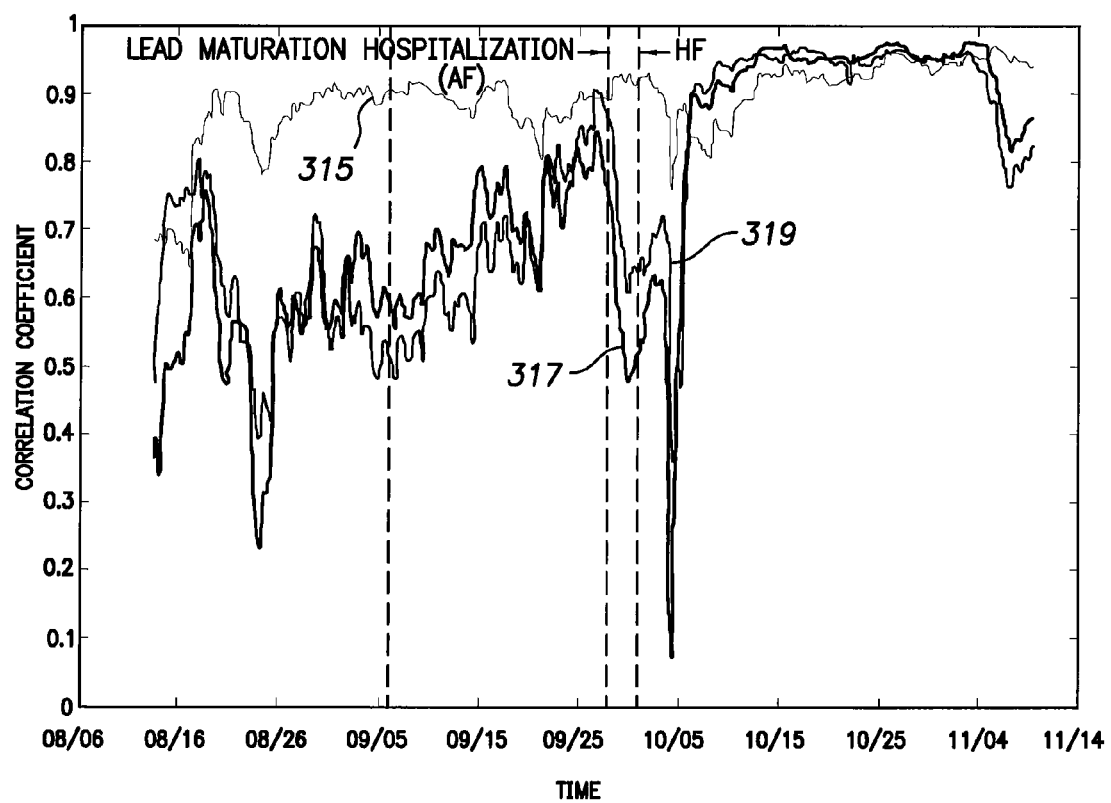
FIG. 7 provides exemplary graphs illustrating changes over time in the information content of impedance vectors for a patient with heart failure.

FIG. 7 illustrates the (non-accumulated) correlation coefficients r for each of the three preferred LV ring-based vector combinations for a second patient. More specifically, graph 315 illustrates $r_1$ for the "LV ring to RV ring vs. LV ring to Case" combination. Graph 317 illustrates $r_2$ for the "LV ring to RA ring vs. LV ring to RV ring" combination. Graph 319 illustrates $r_3$ for the "LV ring to RA ring vs. LV ring to Case" combination. This patient was hospitalized on September 28th of the year shown due to atrial fibrillation, which led to the onset of heart failure (on or about October 1st) and a subsequent exacerbation of heart failure (on or about October 4th.) The correlation coefficient for the "LV ring to RA ring vs. LV ring to Case" configuration (i.e. graph 319) dropped from 90% to 60% several days before the October 4th heart failure exacerbation (where the coefficient dropped even more significantly.) During that same period of time prior to the October 4th heart failure exacerbation, the correlation coefficient for the "LV ring to RA ring vs. LV ring to RV ring" configuration (i.e. graph 317) dropped from 85% to 48%. Although FIG. 7 does not specifically illustrate a combined index, it can be appreciated that an index representative of a combination of the three coefficients $r_1$, $r_2$ and $r_3$ would likewise drop significantly prior to the October 4th heart failure exacerbation. Note that, due to eventual hemodynamic stabilization within the patient, the correlation coefficients for the patient subsequently increased despite the continued presence of heart failure.

Hence, correlation coefficients representative of the amount of independent informational content along selected impedance vectors can be used for early detection of heart failure, in at least some cases. That is, as shown in FIG. 7, the correlation coefficients drop significantly before a heart failure exacerbation, as well as during the heart failure exacerbation. In this regard, for the patient of FIG. 7, if a detection technique had instead been used that directly exploited impedance signals (rather than the cross-correlation of impedance signals), heart failure might not have been detected until the October 4th exacerbation. The use of cross-correlation helps ensure that heart failure is detected earlier, thus allowing for prompt medical attention.

Intuitively, the cross-correlation process can be understood by considering that each of the three data groups, or vectors, above contain their own independent information (e.g. LA volumetric information in the LV ring to RA ring vector, ventricular volumetric information in the LV ring to RV ring vector and lung fluid information in the LV ring to Case vector) and a certain level of common information. In a healthy or stable subject, the correlation coefficients trend within a stable range (as shown in FIG. 6), mainly the common/haemostatic status of the patient. However, when heart failure aggravates, the equilibrium is temporarily broken and the independent content of each vector becomes predominant (as shown in FIG. 7.) Independent vectors have a poor correlation coefficient. As such, the inter-vector correlation state degrades as the patient's HF condition worsens.

Returning to FIG. 3, at step 210, the pacer/ICD compares the current values of the index generated at step 208 against one or more thresholds representative of (1) the onset of heart failure, (2) the progression of heart failure, and/or (3) heart failure reaching a critical stage. For example, if the index falls below an initial heart failure detection threshold, the onset of heart failure is thereby automatically detected. A second threshold may be set to a lower value to detect heart failure reaching a more critical stage (i.e. an exacerbation of heart failure). As noted, due to hemodynamic stabilization, the index is expected to increase despite the continued presence of heart failure (as shown in FIG. 7.) Hence, a subsequent significant drop in the index may then be used to detect the subsequent progression of heart failure.

Alternatively, rather than comparing a combined index against one or more thresholds, each of the individual coefficients (or some subset of the individual coefficients) may be separately compared to the threshold(s), with heart failure indicated if any one of the coefficients drops below the threshold(s) or if some predetermined number of the coefficients drops below the threshold(s). For example, an initial heart failure detection threshold may be set to about 60% for separate comparison against each of the three coefficients. For the patient of FIG. 6, none of the coefficients would fall below the 60% threshold and so heart failure would not be detected. For the patient of FIG. 7, two of the individual coefficients would fall below the 60% threshold and so heart failure would be detected. Note also that, by setting the threshold to 60%, heart failure would be detected within the patient of FIG. 7 several days before the subsequent and more severe heart failure exacerbation. That is, early detection is provided. In addition, it should be understood that, depending on how the coefficients and/or indices are calculated, thresholds may be specified so that the coefficients and/or indices need to exceed the threshold, rather than fall below the threshold, to indicate heart failure detection.

In any case, by exploiting a correlation coefficient (representative of the amount of independent informational content within impedance vector signals), various advantages are realized. For example, the correlation coefficient is independent from the impedance baseline of an impedance configuration. That is, low impedance does not affect the correlation coefficients. Also, the correlation coefficient typically drops more significantly (by more than 30%) during a heart failure exacerbation, as compared with a 10-15% drop in impedance measurements. As such, it is easier to detect heart failure by exploiting the correlation coefficient than with detection techniques that instead exploit the impedance measurements directly. Still further, as shown, the use of the impedance-based correlation coefficient may allow for early detection of heart failure.

Depending upon the capabilities of the pacer/ICD, the detection of heart failure made at step 210 of FIG. 3 may be corroborated by other suitable detection techniques. See, for example, U.S. Pat. No. 6,922,587, entitled "System and Method for Tracking Progression of Left Ventricular Dysfunction Using Implantable Cardiac Stimulation Device"; U.S. Pat. No. 6,942,622, entitled "Method For Monitoring Autonomic Tone"; U.S. Pat. No. 6,748,261, cited above; U.S. Pat. No. 6,741,885, entitled "Implantable Cardiac Device for Managing the Progression of Heart Disease and Method"; U.S. Pat. No. 6,643,548, entitled "Implantable Cardiac Stimulation Device for Monitoring Heart Sounds to Detect Progression and Regression of Heart Disease and Method Thereof"; U.S. Pat. No. 6,572,557, entitled "System and Method for Monitoring Progression of Cardiac Disease State Using Physiologic Sensors"; U.S. Pat. No. 6,527,729, entitled "Method for Monitoring Patient Using Acoustic Sensor"; U.S. Pat. No. 6,512,953, entitled "System and Method for Automatically Verifying Capture During Multi-Chamber Stimulation"; and U.S. Pat. No. 6,480,733, entitled "Method for Monitoring Heart Failure"; each assigned to Pacesetter, Inc. See, also, U.S. Pat. No. 7,272,443, of Bornzin et al., entitled "System and Method for Predicting a Heart Condition Based on Impedance Values Using an Implantable Medical Device"; and U.S. Pat. No. 7,094,207, entitled "System and Method for Diagnosing and Tracking Congestive Heart Failure Based on the Periodicity of Cheyne-Stokes Respiration Using an Implantable Medical Device"; and U.S. patent application Ser. No. 11/397,066 of Koh, entitled "QT-Based System and Method for Detecting and Distinguishing Dilated Cardiomyopathy and Heart Failure Using an Implantable Medical Device," also assigned to Pacesetter, Inc.

At step 212 of FIG. 3, if no heart failure is detected, processing returns to step 202 for continued tracking of impedance signals. However, if heart failure is detected, then, at step 214, the pacer/ICD generates warning signals, stores diagnostic information, and controls pacing, as already discussed. The diagnostics information may include trending information representative of the progression of heart failure within the patient.

In some examples, the above-described impedance parameters are measured and compared only while the patient is at rest, for consistency. A sleep or circadian detector may be used to identify appropriate periods of time to measure the impedance values. Any of a variety of otherwise conventional sleep detection techniques may be employed. Examples are set forth in the following patents or patent applications: U.S. Pat. No. 5,476,483, to Bornzin et al., entitled "System and Method for Modulating the Base Rate During Sleep for a Rate-responsive Cardiac Pacemaker"; U.S. Pat. No. 6,128,534 to Park et al., entitled "Implantable Cardiac Stimulation Device and Method for Varying Pacing Parameters to Mimic Circadian Cycles"; and in U.S. Pat. No. 7,207,947, of Koh et al., entitled "System and Method for Detecting Circadian States Using an Implantable Medical Device." In addition, posture detectors may be used to determine when the patient is in a certain predetermined posture (such as supine) so as to reduce or eliminate any variations in the measurement of the impedance values that may be due to changes in posture. See, e.g., posture detection techniques described in U.S. Pat. No. 6,658,292 of Kroll et al., entitled "Detection of Patient's Position and Activity Status Using 3D Accelerometer-Based Position Sensor." See, also, U.S. Pat. No. 7,149,579, of Koh et al., entitled "System and Method for Determining Patient Posture Based on 3-D Trajectory Using an Implantable Medical Device."

What have been described are various techniques for detecting heart failure or other conditions based on the information content of physiological signals and for controlling therapy and other functions in response thereto. For the sake of completeness, a detailed description of an exemplary pacer/ICD for controlling these functions will now be provided. However, principles of invention may be implemented within other pacer/ICD implementations or within other implantable devices. Furthermore, although examples described herein involve processing of the various signals by the implanted device itself, some operations may be performed using an external device, such as a device programmer, computer server or other external system. For example, recorded impedance data may be transmitted to an external device, which processes the data to evaluate heart failure. Processing by the implanted device itself is preferred as that allows prompt warnings in response to detection of the onset of heart failure.

Exemplary Pacemaker/ICD

Figure 8:
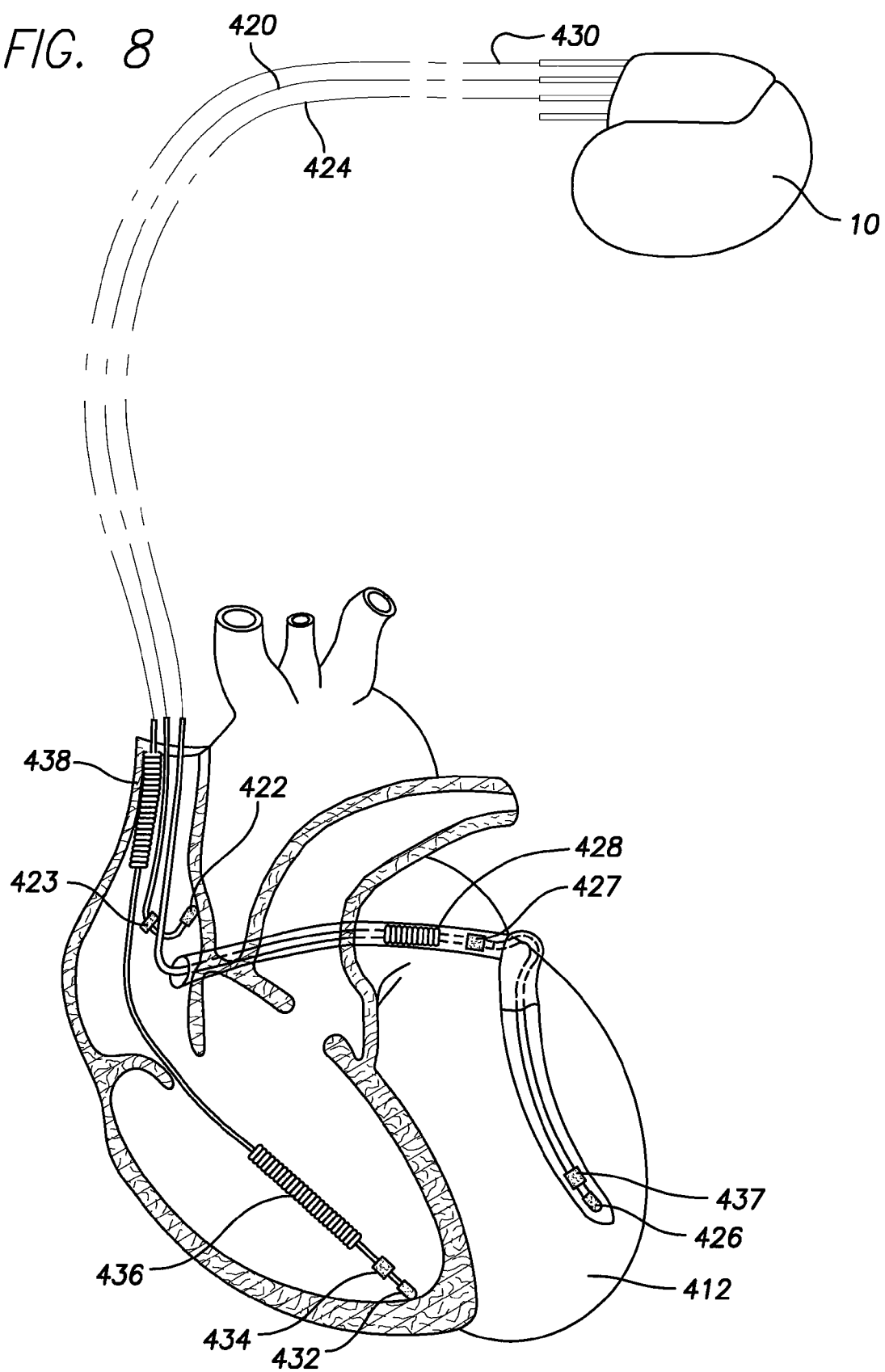
FIG. 8 is a simplified, partly cutaway view, illustrating the pacer/ICD of FIG. 1 along with a more complete set of exemplary leads implanted in the heart of a patient.
Figure 9:
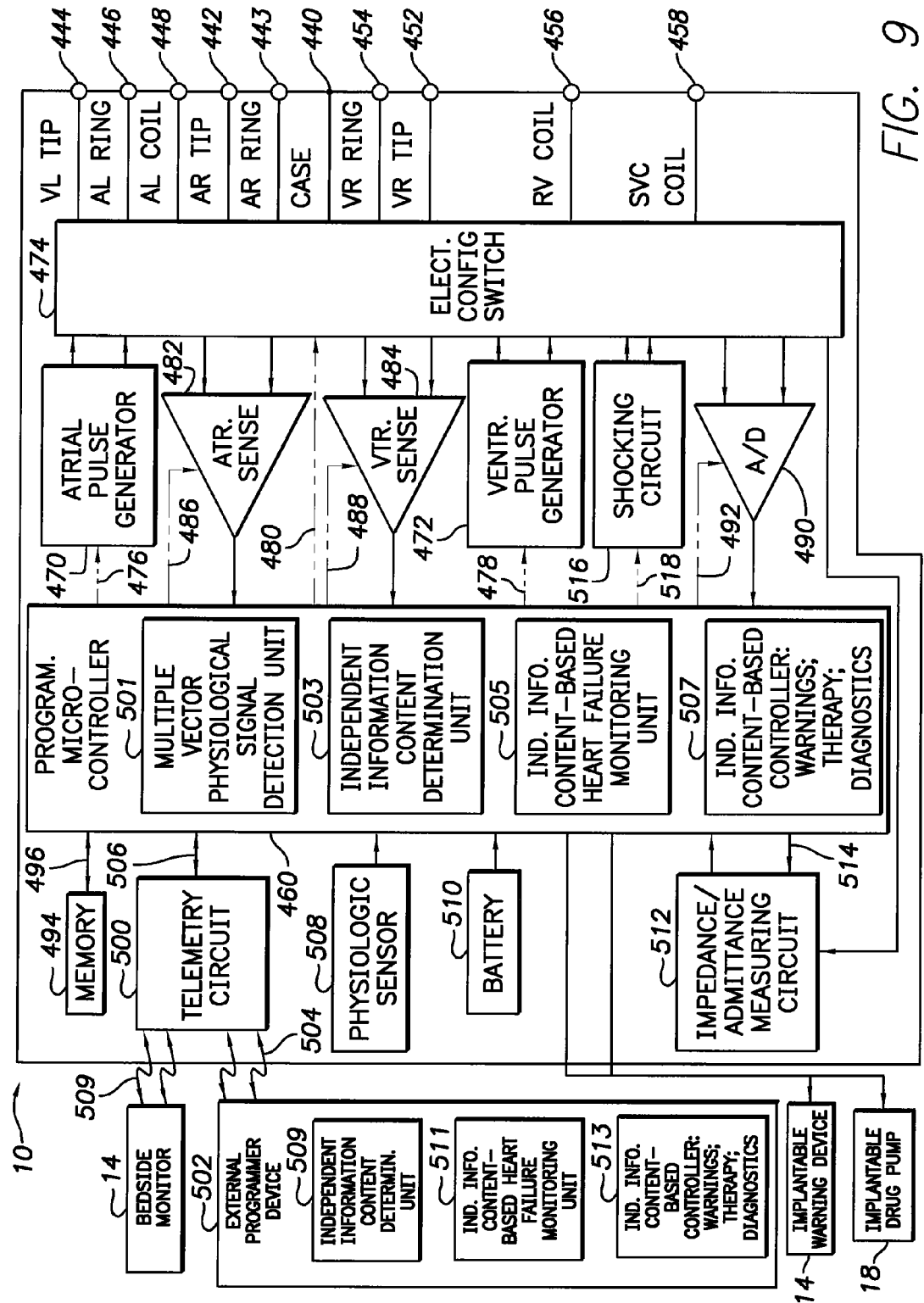
FIG. 9 is a functional block diagram of the pacer/ICD of FIG. 8 and of an external device programmer, illustrating basic device circuit elements that provide cardioversion, defibrillation and/or pacing stimulation in four chambers of the heart and particularly illustrating components within the device or within the external system for detecting heart failure based changes in the information content of immittance vectors within the patient and for controlling warnings, diagnostics and therapy in response thereto.

With reference to FIGS. 8 and 9, a description of an exemplary pacer/ICD will now be provided. FIG. 8 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 6, it should also be understood that additional stimulation leads (with one or more pacing, sensing and/or shocking electrodes) might be used in order to efficiently and effectively provide pacing stimulation to the left side of the heart or atrial cardioversion and/or defibrillation.

A simplified block diagram of internal components of pacer/ICD 410 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned AF detection.

The housing 440 for pacer/ICD 410, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control and/or automatic sensitivity control, bandpass filtering, and a threshold detection circuit, as known in the art, to selectively sense the cardiac signal of interest. The automatic gain/sensitivity control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AV delay, V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

The pacer/ICD additionally includes a battery 510, which provides operating power to all of the circuits shown in FIG. 9. The battery 510 may vary depending on the capabilities of pacer/ICD 410. For pacer/ICD 410, which employs shocking therapy, the battery 510 should be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 9, pacer/CD 410 is shown as having an impedance measuring circuit 512 which is enabled by the microcontroller 460 via a control signal 514. Additionally or alternatively, impedance/admittance measuring circuit may be equipped to measure other related parameters, such as conductance. As explained, impedance/admittance may be used to detect heart failure or other medical conditions. Other uses for an impedance/admittance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; and detecting the opening of heart valves, etc. The impedance/admittance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 or more joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 or more joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

Insofar as heart failure detection is concerned, the microcontroller includes a multiple vector physiological signal detection unit 501, which is operative to sense, detect or measure physiological signals within the patient along a plurality of different vectors. The vectors may be selected using switch 74. In the case of impedance/admittance signals, measuring circuit 512 may also be employed. The microcontroller also includes an on-board independent information content determination unit 503, which is operative to determine an amount of independent informational content among the physiological signals of the different vectors using techniques described above. An on-board independent information content-based heart failure monitoring unit 505 is provided to detect heart failure or other medical conditions based on the amount of independent informational content among physiological signals of the different vectors, as described above. An on-board independent information content-based controller 507 is provided to control at least one pacer/ICD device function based on the amount of independent informational content among physiological signals of the different vectors, as also described above. Such functions can include, e.g.: the generation of warning signals via implantable warning device 14, if provided; the control of therapy (including control of an implantable drug pump 18, if provided); the generation of diagnostics data (including trend information) for storage within memory 494 or elsewhere. Controller 507 also controls the telemetry circuit to send appropriate warning signals via communication link 507 to the bedside monitor 18 or external programmer 502. Note that implantable warning device 14 and implantable drug pump 18 are shown as being functionally connected to the microcontroller. If these devices are external to the pacer/ICD housing, then suitable terminals may be provided on the pacer/ICD housing for inputting/outputting signals to the devices.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

The external device programmer (or other external system) may also include: an independent information content determination unit 509 operative to determine an amount of independent informational content among the physiological signals of the different vectors based on data received from the implanted device; an independent information content-based heart failure monitoring unit 511 to detect heart failure or other medical conditions based on the amount of independent informational content among physiological signals of the different vectors; and an independent information content-based controller 513 provided to control at least one pacer/ICD device function based on the amount of independent informational content among physiological signals of the different vectors. Such functions can include, e.g.: the generation of warning signals; the control of therapy (including transmission of therapy control signals to the implanted device); the generation of diagnostics data (including trend information), etc. In still other implementations, some of these components will only be included within the implanted device, whereas others will be included only within one or more external systems. As noted, the external system can incorporate such devices as device programmers, beside monitors, computer servers or websites. As can be appreciated, there is a wide variety of possible implementations.

The principles of the invention may be exploiting using other implantable systems or in accordance with other techniques. Thus, while the invention has been described with reference to particular exemplary embodiments, modifications can be made thereto without departing from scope of the invention. The various functional components of the exemplary systems described herein may be implemented using any appropriate technology including, for example, microprocessors running software programs or ASICs executing hard-wired logic operations. Note also that the term "including" as used herein is intended to be inclusive, i.e. "including but not limited to."

What is claimed is:

1. A method for use with an implantable medical device for implant within a patient, the method comprising:
   sensing physiological signals within the patient along a plurality of different vectors;
   determining an inter-vector cross-correlation coefficient from the plurality of different vectors;
   determining an amount of independent informational content from the inter-vector cross-correlation coefficient; and
   controlling at least one function based on the amount of independent informational content among the physiological signals of the different vectors.

2. The method of claim 1 wherein sensing physiological signals includes sensing immittance signals.

3. The method of claim 2 wherein sensing immittance signals includes sensing one or more of impedance or admittance signals along a plurality of different vectors within the thorax of the patient.

4. The method of claim 3 wherein at least one of the plurality of vectors passes through the heart of the patient.

5. The method of claim 4 wherein the plurality of vectors include one or more of: LV ring to RA ring, LV ring to RV ring, and LV ring to Case vectors.

6. The method of claim 4 wherein
   determining an inter-vector cross-correlation coefficient comprises determining an inter-vector cross-correlation coefficient from the immittance signals among the different vectors and wherein determining an amount of independent informational content comprises determining the amount of independent informational content from the inter-vector cross-correlation coefficient.

7. The method of claim 6 wherein the correlation coefficient is determined so that a decrease in the correlation coefficient is representative of an increase in the independent informational content among physiological signals of the different vectors.

8. The method of claim 7 wherein the different vectors are selected so that a decrease in the correlation coefficient is representative of a change in hemodynamic equilibrium within the patient.

9. The method of claim 7 wherein the different vectors are selected so that a decrease in the correlation coefficient is representative of deterioration of at least one physiological condition affecting hemodynamic equilibrium.

10. The method of claim 9 wherein the different vectors are selected so that a decrease in the correlation coefficient is representative of heart failure.

11. The method of claim 10 further including:
    comparing the correlation coefficient against a predetermined threshold; and
    detecting heart failure if the correlation coefficient falls below the threshold.

12. The method of claim 11 wherein a plurality of correlation coefficients are determined based on a plurality of groups of immittance signals and wherein heart failure is detected if a predetermined number of correlation coefficients falls below the threshold.

13. The method of claim 11 wherein a plurality of correlation coefficients are determined based on a plurality of groups of immittance signals and wherein the heart failure is detected if an index based on a predetermined numerical combination of the correlation coefficients falls below the threshold.

14. The method of claim 13 wherein the index is representative of an accumulated change in one or more correlation coefficients.

15. The method of claim 6 wherein determining the cross-correlation coefficient from the immittance signals among the different vectors includes calculating:

$$r = \frac{n\sum xy - (\sum x)(\sum y)}{\sqrt{n(\sum x^2) - (\sum x)^2} \sqrt{n(\sum y^2) - (\sum y)^2}}$$

where n is representative of a number of pairs of data within the immittance signals, and where x and y are representative of immittance signal data.

16. The method of claim 6 wherein determining the cross-correlation coefficient from the immittance signals among the different vectors is performed over a predetermined interval of time.

17. The method of claim 1 wherein controlling at least one function includes generating a signal indicative of detection of a medical condition based on a change in the amount of independent informational content among the physiological signals of the different vectors.

18. The method of claim 1 wherein controlling at least one function further includes generating a warning signal indicative of a significant increase in the amount of independent informational content among the physiological signals of the different vectors.

19. The method of claim 1 wherein controlling at least one function includes generating diagnostic information representative of the amount of independent informational content among the physiological signals of the different vectors.

20. The method of claim 19 wherein the amount of independent informational content among physiological signals of the different vectors is representative of deterioration of heart failure and wherein the diagnostic information include heart failure trend information.

21. The method of claim 1 wherein controlling at least one function includes controlling the delivery of therapy based on the amount of independent informational content among the physiological signals of the different vectors.

22. The method of claim 1 wherein the steps are performed by the implantable medical device.

23. The method of claim 1 wherein some of the steps are performed by the implantable medical device and others are performed by an external system.

24. The method of claim 23 wherein the step of sensing physiological signals within the patient along a plurality of different vectors is performed by the implantable medical device and wherein the steps of determining the amount of independent informational content and controlling at least one function based on the amount of independent informational content are performed by an external device based on physiological signals sensed within the patient and transmitted to the external device.

25. A system for use with an implantable medical device for implant within a patient, the system comprising:
a multiple vector physiological signal detection unit operative to sense physiological signals within the patient along a plurality of different vectors; and
an independent information content determination unit operative configured to determine an inter-vector cross-correlation coefficient from the plurality of different vectors; and
a controller operative to control at least one function based on the inter-vector cross-correlation coefficient.

26. The system of claim 25 wherein the multiple vector physiological signal detection unit, the independent information content determination unit, and the controller are components of the implantable medical device.

27. The system of claim 25 wherein some of the components of the system are components of the implantable medical device and others are components of an external system.

28. The system of claim 27 wherein the multiple vector physiological signal detection unit is a component of the implantable medical device and the independent information content determination unit and the controller are components of an external system.

29. The system of claim 27 wherein the external system comprises one or more of a device programmer, a bedside monitor, a computer server and a website.

30. The system of claim 25 wherein the amount of independent informational content among physiological signals of the different vectors is representative of heart failure and wherein the controller is operative to generate a warning signal indicative of heart failure.

31. A system for use with an implantable medical device for implant within a patient, the system comprising:
means for sensing physiological signals within the patient along a plurality of different vectors;
means for determining an inter-vector cross-correlation coefficient from the plurality of different vectors;
means for determining an amount of independent informational content from the inter-vector cross-correlation coefficient; and
means for controlling at least one function based on the amount of independent informational content among physiological signals of the different vectors.

* * * * *